United States Patent [19]
Matsui et al.

[11] Patent Number: 5,855,814
[45] Date of Patent: Jan. 5, 1999

[54] LIQUID CRYSTAL COMPOSITIONS AND LIQUID CRYSTAL DISPLAY ELEMENTS

[75] Inventors: Shuichi Matsui; Tomoyuki Kondo; Kazutoshi Miyazawa, all of Ichihara; Noriyuki Ohnishi, Tsukuba; Yasuyuki Goto, Ichihara; Etsuo Nakagawa, Ichihara; Shinichi Sawada, Ichihara, all of Japan

[73] Assignee: Chisso Corporation, Osaka, Japan

[21] Appl. No.: 875,947

[22] PCT Filed: Feb. 7, 1996

[86] PCT No.: PCT/JP96/00257

§ 371 Date: Aug. 11, 1997

§ 102(e) Date: Aug. 11, 1997

[87] PCT Pub. No.: WO96/24649

PCT Pub. Date: Aug. 15, 1996

[30] Foreign Application Priority Data

Feb. 9, 1995 [JP] Japan ................................... 7-046353
Jun. 27, 1995 [JP] Japan ................................... 7-184933

[51] Int. Cl.$^6$ .......................... C09K 19/20; C09K 19/30; C09K 19/12; G02F 1/13
[52] U.S. Cl. .............................. 252/299.67; 252/299.63; 252/299.66
[58] Field of Search .................. 252/299.67, 299.63, 252/299.66

[56] References Cited

U.S. PATENT DOCUMENTS

| | | | |
|---|---|---|---|
| 5,397,505 | 3/1995 | Rieger et al. | 252/299.67 |
| 5,409,637 | 4/1995 | Rieger et al. | 252/299.63 |
| 5,480,581 | 1/1996 | Plach et al. | 252/299.63 |
| 5,543,077 | 8/1996 | Rieger et al. | 252/299.63 |
| 5,560,865 | 10/1996 | Nakagawa et al. | 252/299.01 |
| 5,645,759 | 7/1997 | Tomi et al. | 252/299.63 |
| 5,650,093 | 7/1997 | Hachiya et al. | 252/299.63 |
| 5,653,912 | 8/1997 | Nakagawa et al. | 252/299.01 |
| 5,683,624 | 11/1997 | Sekiguchi et al. | 252/299.61 |
| 5,725,799 | 3/1998 | Bremer et al. | 252/299.67 |
| 5,733,477 | 3/1998 | Kondo et al. | 252/299.67 |

FOREIGN PATENT DOCUMENTS

| | | |
|---|---|---|
| 2 233626 A | 9/1990 | Japan . |
| 6 220454 A | 8/1994 | Japan . |
| 6 248268 A | 9/1994 | Japan . |
| 6 316540 A | 11/1994 | Japan . |
| 7 316082 A | 12/1995 | Japan . |
| WO 9403558 A | 2/1994 | WIPO . |
| WO 9426838 A | 11/1994 | WIPO . |

OTHER PUBLICATIONS

"The Optical Properties of Twisted Nematic Liquid Crystal Structures with Twist Angles< 90°" C.H Gooch, J. Phys. D: Appl. Phys., vol. 8, 1975, 1575–1584.

Invited Address: Advances in Liquid Crystals for TFT Displays, R. Tarao, 223–236, SID 94 Digest, Chisso Petrochemical Corp., Chiba, Japan.

*Primary Examiner*—C. H. Kelly
*Attorney, Agent, or Firm*—Oblon, Spivak, McClelland, Maier & Neustadt, P.C.

[57] ABSTRACT

A liquid crystal composition which comprises as a first component at least one or more compounds represented by formula (1')

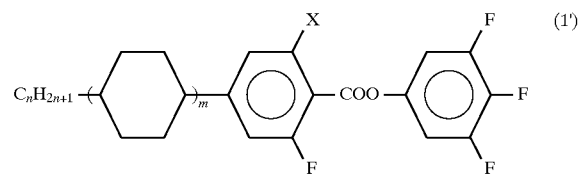

wherein n represents an integer of 1–10; X represents H or F; or m represents 1 or 2 and as a second component at least one or more compounds represented by formulas (2-1) to (2-5) in which n represents an integer of 1–10.

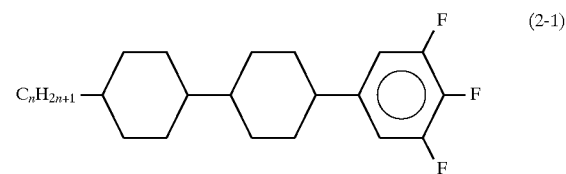

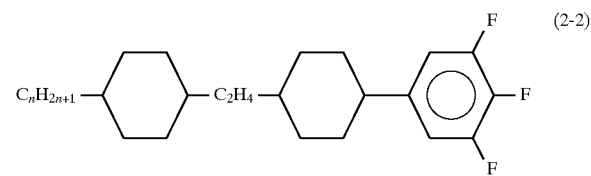

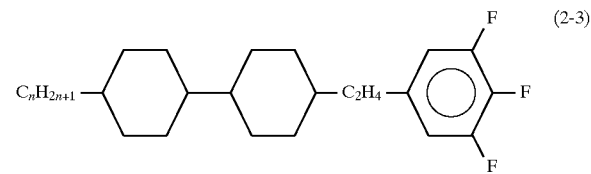

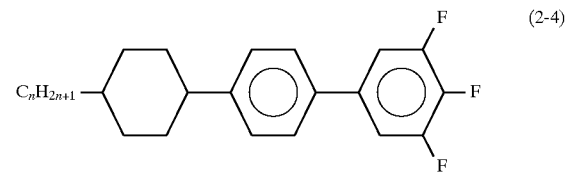

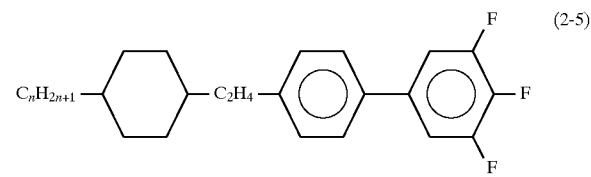

19 Claims, No Drawings

LIQUID CRYSTAL COMPOSITIONS AND LIQUID CRYSTAL DISPLAY ELEMENTS

TECHNICAL FIELD

This invention relates to nematic liquid crystal compositions used in a closed cell composed of two substrates having a transparent electrode and liquid crystal display elements using the liquid crystal compositions.

More particularly, the invention relates to liquid crystal compositions for an active matrix, liquid crystal display element and liquid crystal display elements using said compositions.

BACKGROUND ART

A variety of liquid crystal display elements (LCD) including a twisted nematic (TN) mode, a super twisted nematic (STN) mode, a thin-film transistor (TFT) mode or the like have been put to practical use, because of having lower power consumption, permitting smaller and lighter as compared with a CRT (cathode-ray tube mode display). Among them, an active-matrix LCD (AM-LCD) such as TFT or the like are getting colored and sophisticated, to which attention has been drawn as a prospective flat display.

The characteristics required for the liquid crystal compositions for AM-LCD are recited below.
1) A voltage holding ratio (V.H.R.) is high to maintain high contrast of LCD.
2) A nematic liquid crystal phase range is broad depending on the environment in which the liquid crystal composition is used.
3) A suitable optical anisotropy ($\Delta n$) is acceptable depending on the cell thickness; and
4) A suitable threshold voltage is acceptable depending on the driver.

As an operation system for AM-LCD, a TN display system is employed in which the alignment of a liquid crystalline molecule in the upper and lower substrates is twisted 90°. According to the report by C. H. Gooch and H. A. Tarry in Appl. Phys., Vol. 8, pp. 1575–1584 (1975), the TN display system requires to set a product $\Delta n \cdot d$ of an optical anisotropy ($\Delta n$) and a cell thickness (d)$\mu$m at a predetermined value (e.g., $\Delta n \cdot d = 0.5$ $\mu$m) in order to prevent coloration due to the interference of liquid crystal cell when no voltage is applied, thereby obtaining an optimum contrast. The $\Delta n$ of the liquid crystal composition for TFT which is now put to practical use under such limitation ranges from about 0.07 to about 0.11, principally 0.08 to 0.10, for a cell operating near at the first minimum point of the transmission described in the above reference.

In recent years, the application of LCD has been extensive with the development of a notebook type personal computer which is characterized by small size, light weight and portability. LCD for the purpose of portability undergoes the restriction of characteristics by a driving power sourse. Since the long-term use requires a lower power consumption, a liquid crystal composition having a low threshold voltage is demanded. Further, liquid crystals having a low threshold voltage are required to achieve lighther weight and lower cost of the driving power sourse.

With the portability, the development has been considered for the purpose of outdoor use. To make liquid crystals tolerable to outdoor use, it is required that they exhibit a nematic phase in the ranges exceeding the temperature range under use environment. In such circumstances, the liquid crystal compositions for TFT which are now put to practical use have a nematic phase transition temperature wherein the upper limit (clearing point $T_{NI}$) is not lower than 60° C. and the lower limit ($T_L$) is not higher than −20° C.

In such background, Japanese Patent Kokai 2-233626 discloses trifluoro compounds having a relatively high dielectric anisotropy ($\Delta \epsilon$), in which Example 2 illustrates a composition comprising 15% by weight of a trifluoro compound and 85% by weight of a difluoro compound, but the composition has the problems of high threshold voltage, poor compatibility at lower temperature and narrow nematic phase range.

WO 94/03558 discloses a composition comprising trifluoro and difluoro compounds. The compositions illustrated in Examples 1 and 2 are low in the threshold voltage, but have the problems that the clearing point is not higher than 50° C. and $\Delta n$ is not higher than 0.06.

Thus, the liquid crystal compositions have been investigated according to various purposes, and under the present circumstances, new improvement has been required.

DISCLOSURE OF THE INVENTION

An object of the invention is to provide liquid crystal compositions having in particular, a low threshold voltage, an excellent compatibility at low temperature and a broad nematic phase range, while fulfilling various characteristics required for the liquid crystal compositions for said AM-LCD.

We have investigated compositions using various liquid crystal compounds in an effort to solve the above problems and found that the object of the invention can be achieved by using the present liquid crystal compositions in AM-LCD.

The present invention is fully explained below.

The present invention relates to nematic liquid crystal compositions comprising a compound of formula (1') in which $R_1$ is a straight-chain alkyl group of 1–10 carbons; A and B are a trans-1,4-cyclohexylene; m is 0 or 1 and n is 1; among the phenyl benzoate derivatives of formula (1)

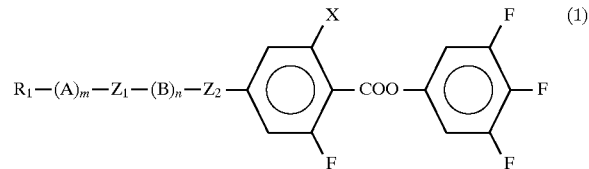

wherein $R_1$ is hydrogen or a straight or branched-chain alkyl group of 1–10 carbons, one or two non-adjacent $CH_2$ groups of which can be substituted by oxygen or —CH=CH—; X represents hydrogen or halogen; A and B each independently represent a 1,4-phenylene or a trans-1,4-cyclohexylene, which may be substituted by halogen; $Z_1$ and $Z_2$ each independently represent —$CH_2CH_2$—, —CO—O—, —O—CO—, —CH=CH—, —C≡C—, —(CH$_2$)$_4$— or a covalent bond; and m and n each independently stand for 0 or 1, and also relates to liquid crystal display elements using said liquid crystal compositions.

In the first aspect, the invention relates to liquid crystal compositions which comprise as a first component at least one or more compounds represented by formula (1')

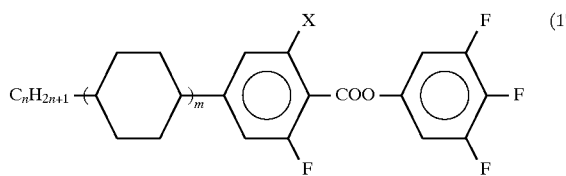

(1')

wherein n represents an integer of 1–10; X represents H or F; or m represents 1 or 2, and as a second component at least one or more compounds represented by formulas (2-1) to (2-5) in which n represents an integer of 1–10.

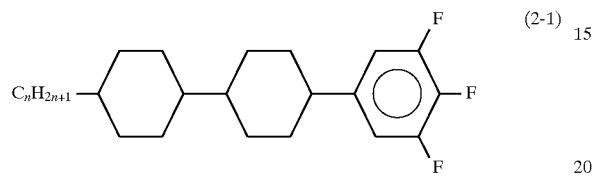

(2-1)

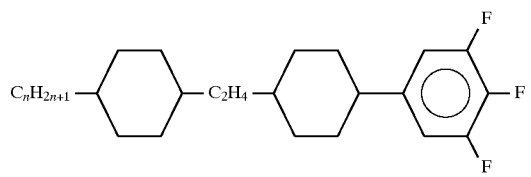

(2-2)

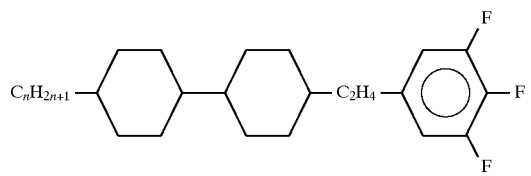

(2-3)

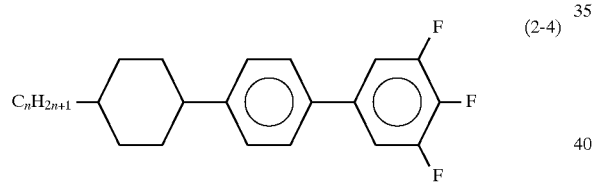

(2-4)

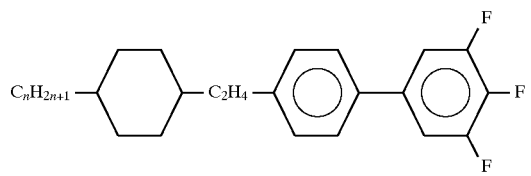

(2-5)

In the second aspect, the invention relates to the liquid crystal compositions as defined in the above first aspect, which comprise 3–40% by weight of the first component and 50–97% by weight of the second component, based on the total weight of the liquid crystal composition.

In the third aspect, the invention relates to the liquid crystal compositions further comprising the compound represented by formula (3-1) and/or formula (3-2)

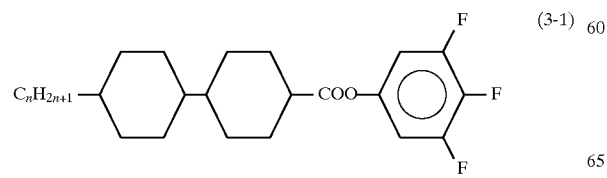

(3-1)

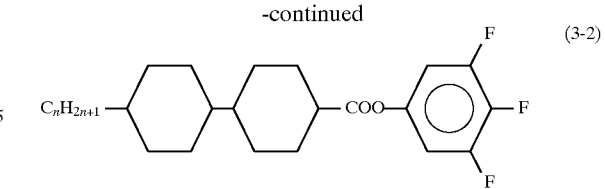

(3-2)

in which n represents an integer of 1–10, in addition to the liquid crystal compositions as defined in the first or second aspect.

In the fourth aspect, the invention relates to the liquid crystal compositions further comprising the compound represented by formula (4)

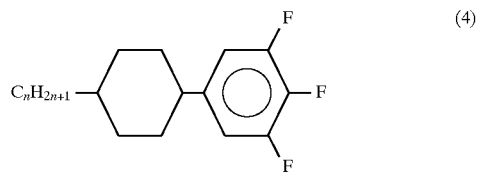

(4)

in which n represents an integer of 1–10, in addition to the liquid crystal compositions as defined in any of the first to third aspects.

In the fifth aspect, the invention relates to the liquid crystal compositions further comprising the compound represented by formula (5-1) and/or formula (5-2)

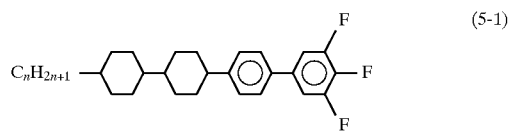

(5-1)

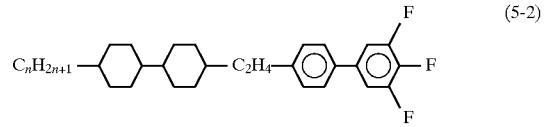

(5-2)

in which n represents an integer of 1–10, in addition to the liquid crystal compositions as defined in any of the first to fourth aspects.

In the sixth aspect, the invention relates to the liquid crystal display elements using the liquid crystal compositions as defined in any of the first to fifth aspects.

The compounds constituting each component of the present invention will be described below.

The compounds represented by formula (1') are new compounds and the processes for the production thereof will be mentioned later.

As the compounds of formula (1') in the present invention, those of the following preferable compounds can be recited, in which n represents an integer of 1–10.

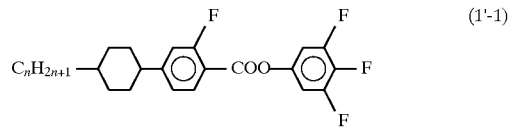

(1'-1)

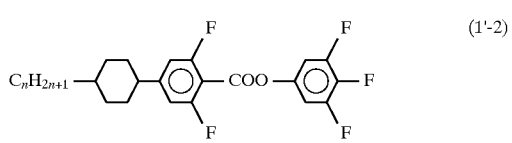

(1'-2)

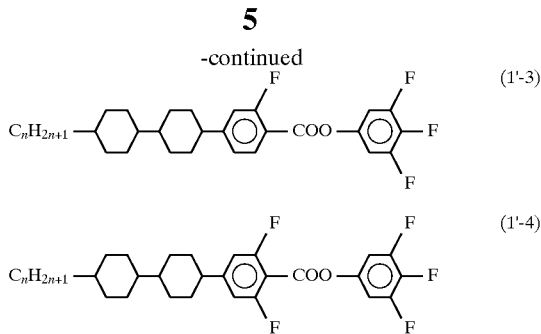

Of those compounds, the compounds represented by formula (1'-1), (1'-2) or (1'-3) are particularly preferably used in the invention.

The compounds of formula (1) in the present invention have high dielectric anisotropy (Δε), excellent thermal and chemical stability, which lead to an reduction in the threshold voltage of the liquid crystal composition, especially for TFT.

With regard to the amount of the first component used, not less than 3% by weight based on the total amount of the liquid crystal composition can exhibit favorably the effect of being capable of driving at low voltage. Not more than 40% by weight offer very good compatibility at low temperature. 5 to 30% by weight are more preferable.

The trifluoro compounds of formulas (2-1) to (2-5), (3-1), (3-2), (4), (5-1) and (5-2) are well known as those for low voltage TFT, as disclosed in Japanese Patent Kokai 2-233626, since they have Δε of about 7–12, a good thermal and chemical stability (R. Tarao et al., SID 94 Digest, p. 233).

The compounds of formulas (2-1) to (2-5) in which the nematic to isotropic transition point (clearing point: $T_{N1}$) ranges from about 50° to 100° C. are optimum compounds as a base compound in the composition for TFT at low voltage.

With regard to the amount of the present second component used, not less than 50% by weight based on the total amount of the liquid crystal composition offer very good compatibility at low temperature. Not more than 97% by weight can exhibit favorably the effect of being capable of driving at low voltage. 60 to 95% by weight are more preferable.

The compounds of formulas (3-1) and (3-2), because of being ester type trifluoro compounds, have high Δε and are preferable for the purpose of more reducing the threshold voltage of the liquid crystal composition.

With regard to the amount of the compounds of formulas (3-1) and (3-2) used, not more than 25% by weight based on the total weight of the liquid crystal composition are preferable from the viewpoint of keeping good the compatibility at low temperature. Not more than 20% by weight are more preferable. The compounds of formula (4), because of being dicyclic trifluoro compounds, are preferable, especially for the purpose of providing more lower the threshold voltage and viscosity of the liquid crystal composition.

With regard to the amount of the compounds of formula (4) used, not more than 15% by weight based on the total weight of the liquid crystal composition are preferable with the viewpoint of keeping the clearing point of the liquid crystal composition at high temperature range. Not more than 10% by weight are more preferable.

The compounds of formulas (5-1) and (5-2), because of being tetracyclic trifluoro compounds, are preferable, especially for the purpose of increasing the clearing point of the liquid crystal composition.

With regard to the compounds of formulas (5-1) and (5-2) used, not more than 20% by weight are preferable with the viewpoint of keeping the threshold voltage low and also keeping good the low temperature compatibility. Not more than 10% by weight are more preferable.

Other compounds than those represented by the above-described formulas can be used in admixture in the compositions of the present invention, within the scope not departing from the objects of the invention.

The liquid crystal compositions of the invention are prepared by processes conventional per se. In general, there are employed the processes wherein various components are dissolved one another at high temperatures. Further, the liquid crystal materials of the present invention are improved and optimized depending on the intended applications by using suitable additives. Such additives are well known to a person skilled in the art and fully described in any references. In general, a chiral dopant is added for inducing helical structures of the liquid crystal to control necessary twist angle and preventing a reverse twist.

Further, the liquid crystal compositions of the present invention can be used as liquid crystal materials for guest-host (GH) mode by incorporating therein dichronic dyes such as merocyanines, styryls, azo, azomethines, azoxy, quinophthalones, anthraquinones, tetrazines or the like. Alternatively, they can be used as liquid crystal materials for NPCA formed by micro-capsulation of nematic liquid crystals, or as liquid crystal materials for polymer dispersion type liquid crystal display elements (PDLCD), a typical example of which is a polymer network liquid crystal display element (PNLCD) wherein a three-dimentional network polymer is formed in the liquid crystal. In addition, they can be used as liquid crystal materials for electrically controlled birefringence (ECB) mode and dynamic scattering (DS) mode.

(Process for the preparation of the compound represented by formula (1'))

The process for the preparation of the compound represented by formula (1') is described below. In the description on the phase transition temperature of each compound, Cr stands for a crystal, N stands for a nematic phase, S stands for a smectic phase, Iso stands for an isotropic liquid and the unit of the phase transition temperature is °C.

Process 1 for the preparation of the compound Preparation of 3,4,5-trifluorophenyl-(2-fluoro-4-(trans-4-propylcyclohexyl)benzoate (the compound of formula (1') wherein n is 3, m is 1 and X is hydrogen)

The reaction steps are separated into two steps of 1) preparation of 2-fluoro-4-(trans-4-propylcyclohexyl) benzoic acid and 2) esterification. Each of the preparation steps is explained below.

1) Preparation of 2-fluoro-4-(trans-4-propylcyclohexyl)benzoic acid

Into a 1 liter, three-necked flask equipped with a thermometer, a cooling tube and a stirrer were charged 400 ml of ethyleneglycol, 40.0 g (163.0 mmol) of 2-fluoro-4-(trans-4-propylcyclohexyl)benzonitrile and an aqueous solution of sodium hydroxide (19.6 g, 489.1 mmol) dissolved in equal amount of water, the mixture was heated to 150° C. and stirred for 10 hrs. The reaction solution was allowed to cool to room temperature with stirring. 200 ml of water and 200 ml of an aqueous solution of 6N hydrochloric acid were added to make the system acid. The precipitated insoluble material was recovered by filtration. The recovered material was sufficiently washed with water, dried under reduced pressure and recrystallized from toluene to afford 30.5 g of a colorless crystalline product which was 2-fluoro-4-(trans-4-propylcyclohexyl)benzoic acid.

2) Preparation of 3,4,5-trifluorophenyl-2-fluoro-4-(trans-4-propylcyclohexyl)benzoate In a three-necked flask equipped with a thermometer, a cooling tube, a dropping funnel and an alkali trap, 20 g (75.7 mmol) of 2-fluoro-4-(trans-4-propylcyclohexyl)benzoic acid obtained in step 1) and 0.3 ml of pyridine were dissolved in 100 ml of toluene. 13.5 g (113.5 mmol) of thionyl chloride were added dropwise to the solution under room temperature over a period of 10 minutes with stirring. After completion of addition, the mixture was heated to 60° C. and stirred for 2 hrs. The reaction solution was cooled to room temperature, unreacted thionyl chloride and toluene was distilled off under reduced pressure by a water jet aspirator and condensed. The residue was distilled under reduced pressure to recover a fraction at bp 158°–160° C./1.0 mHg, thus obtaining 19.2 g of a colorless, oily product, which is 2-fluoro-4-(trans-4-propylcyclohexyl)-acetic acid chloride. Into a 200 ml, three-necked flask equipped with a thermometer, a cooling tube, a dropping funnel and a stirrer were charged 5.2 g (35 mmol) of 3,4,5-trifluorophenol, 3.0 g (38.0 mmol) of pyridine and 20 ml of toluene. To the mixture was added dropwise 2-fluoro-4-(trans-4-propylcyclohexyl)benzoic acid chloride at room temperature with stirring over a period of 15 minutes. After completion of addition, the mixture was heated to 60° C. on a water bath and stirred for 2 hrs. The reaction solution was cooled to room temperature and 100 ml of water was added to complete the reaction. After the toluene layer was separated from the reaction solution, the water layer was extracted with toluene (50 ml×2). The combined organic layer was washed with successive, 50 ml of an aqueous solution of 1N hydrochloric acid, water (50 ml×2), 50 ml of an aqueous solution of saturated sodium hydrogencarbonate and water (50 ml×2), dried over anhydrous magnesium sulfate and concentrated under reduced pressure to afford 23.1 g of brown, crystalline reaction product. The reaction product was treated with a column chromatography using silica gel as a column and toluene as a developing solvent, and recrystallized from heptane to obtain 14.8 g of a colorless, crystalline product which was 3,4,5-trifluorophenyl-(2-fluoro-4-(trans-4-propylcyclohexyl))benzoate, Cr 78.1–79.1(N-Iso 71.1–71.2)Iso.

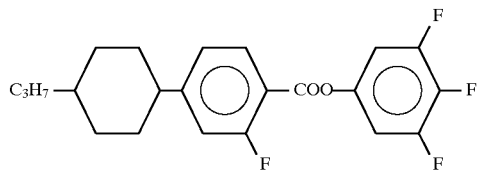

The following 3,4,5-trifluorophenyl-(2-fluoro-4-(trans-4-alkylcyclohexyl))benzoates could be prepared in accordance with the above method by using 2-fluoro-4-(trans-4-alkylcyclohexyl)benzonitrile having different length of the alkyl group, in place of 2-fluoro-4-(trans-4-propylcyclohexyl)benzonitrile.

3,4,5-trifluorophenyl-(2-fluoro-4-(trans-4-methylcyclohexyl))benzoate;
3,4,5-trifluorophenyl-(2-fluoro-4-(trans-4-ethylcyclohexyl))benzoate, Cr 79.3–79.6 Iso;
3,4,5-trifluorophenyl-(2-fluoro-4-(trans-4-butylcyclohexyl))benzoate;
3,4,5-trifluorophenyl-(2-fluoro-4-(trans-4-pentylcyclohexyl))benzoate, Cr 73.8–74.7N 85.0–85.1 Iso;
3,4,5-trifluorophenyl-(2-fluoro-4-(trans-4-hexylcyclohexyl))benzoate;
3,4,5-trifluorophenyl-(2-fluoro-4-(trans-4-heptylcyclohexyl))benzoate;
3,4,5-trifluorophenyl-(2-fluoro-4-(trans-4-octylcyclohexyl))benzoate;
3,4,5-trifluorophenyl-(2-fluoro-4-(trans-4-nonylcyclohexyl))benzoate;
3,4,5-trifluorophenyl-(2-fluoro-4-(trans-4-decylcyclohexyl))benzoate.

The following 3,4,5-trifluorophenyl-(2,6-difluoro-4-(trans-4-alkylcyclohexyl))benzoates could be prepared in accordance with the above method by using 2,6-difluoro-4-(trans-4-alkylcyclohexyl)benzonitrile, in place of 2-fluoro-4-(trans-4-propylcyclohexyl)benzonitrile.

3,4,5-trifluorophenyl-(2,6-difluoro-4-(trans-4-methylcyclohexyl))benzoate;
3,4,5-trifluorophenyl-(2,6-difluoro-4-(trans-4-ethylcyclohexyl))benzoate;
3,4,5-trifluorophenyl-(2,6-difluoro-4-(trans-4-propylcyclohexyl))benzoate;
3,4,5-trifluorophenyl-(2,6-difluoro-4-(trans-4-butylcyclohexyl))benzoate;
3,4,5-trifluorophenyl-(2,6-difluoro-4-(trans-4-pentylcyclohexyl))benzoate Cr 76.8–77.1(N 63.1–63.8) Iso;
3,4,5-trifluorophenyl-(2,6-difluoro-4-(trans-4-hexylcyclohexyl))benzoate;
3,4,5-trifluorophenyl-(2,6-difluoro-4-(trans-4-heptylcyclohexyl))benzoate;
3,4,5-trifluorophenyl-(2,6-difluoro-4-(trans-4-octylcyclohexyl))benzoate;
3,4,5-trifluorophenyl-(2,6-difluoro-4-(trans-4-nonylcyclohexyl))benzoate;
3,4,5-trifluorophenyl-(2,6-difluoro-4-(trans-4-decylcyclohexyl))benzoate.

Process 2 for the preparation of the compound
Preparation of 3,4,5-trifluorophenyl-(2-fluoro-4-(trans-4-(trans-4-ethylcyclohexyl)benzoate (the compound of formula (1') wherein n is 2, m is 2 and X is hydrogen)

In a 300 ml, three-necked flask equipped with a thermometer, a cooling tube and a stirrer, 10 g (31.9 mmol) of 2-fluoro-4-(trans-4-(trans-4-ethylcyclohexyl)cyclohexyl)benzonitrile and 5 ml of an aqueous solution of sodium hydroxide (3.2 g, 79.8 mmol) dissolved in equal amount of water were dissolved by heat in 100 ml of ethyleneglycol and the mixture was stirred for 5 hrs, while keeping at 180° C. The solution was cooled to room temperature, 50 ml of water and 20 ml of an aqueous solution of 6N hydrochloric acid were added, and the precipitated crystalline material was recovered by filtration. The recovered material was washed repeatedly with water, dried and recrystallized from toluene to afford 9.8 g of a colorless crystalline product, which is 2-fluoro-4-(trans-4-(trans-4-ethylcyclohexyl)benzoic acid.

In a 300 ml, Kjeldahl flask, 9.8 g (29.3 mmol) of 2-fluoro-4-(trans-4-(trans-4-ethylcyclohexyl)cyclohexyl)benzoic acid were dissolved in 100 ml of toluene, and 0.2 g of pyridine was added to the flask. To the mixture were added dropwise at room temperature 4.5 g (38.1 mmol) of thionyl chloride over a period of 3 minutes with stirring. After completion of addition, the mixture was heated to 60° C. on a hot bath and reacted for 2 hrs, while keeping the same temperature. The reaction solution was subjected to reduced pressure by an aspirator by which an unreacted thionyl chloride and toluene was distilled off, and condensed. The residue was distilled under reduced pressure to afford the acid chloride derivative (8.5 g colorless crystalline material). In a 200 ml, three-necked flask equipped with a nitrogen introducing tube, a thermometer, a dropping funnel and a stirrer, 4.3 g (29.2 mmol) of 3,4,5-trifluorophenol and 2.1 g (26.7 mmol) of pyridine were dissolved in 50 ml of toluene under a nitrogen atomosphere. To the mixture was added dropwise 8.5 g (24.3 mmol) of the acid chloride derivative with stirring over a period of 10 minutes. After completion of addition, the mixture was kept at 60° C. on a hot bath and aged for 2 hrs. To the reaction solution were added 100 ml of water to complete the reaction. After the toluene layer was separated from the reaction solution, the water layer was extracted with 100 ml of diethyl ether. The combined organic layer was washed with successive, 100 ml of water, 50 ml of an aqueous solution of 2N sodium hydrochloride and water (100 ml×2), dried over anhydrous magnesium sulfate and concentrated to afford 9.7 g of a reaction product. The reaction product was purified by a silica gel column chromatography using toluene as a developing solvent, and recrystallized from a toluene-heptane mixed solvent to obtain 5.7 g of a colorless, crystalline product which was 3,4,5-trifluorophenyl-(2-fluoro-4-(trans-4-(trans-4-ethylcyclohexyl)cyclohexyl))benzoate.

The following 3,4,5-trifluorophenyl-(2-fluoro-4-(trans-4-alkylcyclohexyl)cyclohexyl))benzoates could be prepared in accordance with the above method by using 2-fluoro-4-(trans-4-(trans-4-alkylcyclohexyl)cyclohexyl)benzonitrile having different length of the alkyl group, in place of 2-fluoro-4-(trans-4-(trans-4-ethylcyclohexyl)cyclohexyl) benzonitrile.

3,4,5-trifluorophenyl-(2-fluoro-4-(trans-4-(trans-4-methylcyclohexyl)cyclohexyl)benzoate;

3,4,5-trifluorophenyl-(2-fluoro-4-(trans-4-(trans-4-propylcyclohexyl)cyclohexyl))benzoate, Cr 110.1–110.9N 248.9–249.7 Iso;

3,4,5-trifluorophenyl-(2-fluoro-4-(trans-4-(trans-4-butylcyclohexyl)cyclohexyl))benzoate;

3,4,5-trifluorophenyl-(2-fluoro-4-(trans-4-(trans-4-pentylcyclohexyl)cyclohexyl))benzoate;

3,4,5-trifluorophenyl-(2-fluoro-4-(trans-4-(trans-4-hexylcyclohexyl)cyclohexyl)benzoate;

3,4,5-trifluorophenyl-(2-fluoro-4-(trans-4-(trans-4-heptylcyclohexyl)cyclohexyl)benzoate;

3,4,5-trifluorophenyl-(2-fluoro-4-(trans-4-(trans-4-octylcyclohexyl)cyclohexyl))benzoate;

3,4,5-trifluorophenyl-(2-fluoro-4-(trans-4-(trans-4-nonylcyclohexyl)cyclohexyl))benzoate;

3,4,5-trifluorophenyl-(2-fluoro-4-(trans-4-(trans-4-decylcyclohexyl)cyclohexyl)benzoate.

Further, the following 3,4,5-trifluorophenyl-(2,6-difluoro-4-(trans-4-alkylcyclohexyl)cyclohexyl))-benzoates could be prepared in accordance with the above method by using 2,6-difluoro-4-(trans-4-(trans-4-alkylcyclohexyl)cyclohexyl)benzonitrile having different length of the alkyl group, in place of 2-fluoro-4-(trans-4-(trans-4-ethylcyclohexyl) cyclohexyl)benzonitrile.

3,4,5-trifluorophenyl-(2,6-difluoro-4-(trans-4-(trans-4-methylcyclohexyl)cyclohexyl)benzoate;

3,4,5-trifluorophenyl-(2,6-difluoro-4-(trans-4-(trans-4-ethylcyclohexyl)cyclohexyl))benzoate;

3,4,5-trifluorophenyl-(2,6-difluoro-4-(trans-4-(trans-4-propylcyclohexyl)cyclohexyl))benzoate;

3,4,5-trifluorophenyl-(2,6-difluoro-4-(trans-4-(trans-4-butylcyclohexyl)cyclohexyl))benzoate;

3,4,5-trifluorophenyl-(2,6-difluoro-4-(trans-4-(trans-4-pentylcyclohexyl)cyclohexyl))benzoate;

3,4,5-trifluorophenyl-(2,6-difluoro-4-(trans-4-(trans-4-hexylcyclohexyl)cyclohexyl)benzoate;

3,4,5-trifluorophenyl-(2,6-difluoro-4-(trans-4-(trans-4-heptylcyclohexyl)cyclohexyl)benzoate;

3,4,5-trifluorophenyl-(2,6-difluoro-4-(trans-4-(trans-4-octylcyclohexyl)cyclohexyl))benzoate;

3,4,5-trifluorophenyl-(2,6-difluoro-4-(trans-4-(trans-4-nonylcyclohexyl)cyclohexyl))benzoate;

3,4,5-trifluorophenyl-(2,6-difluoro-4-(trans-4-(trans-4-decylcyclohexyl)cyclohexyl)benzoate.

The invention is further illustrated by the following examples, but not limiting thereto. The composition ratio in the Comparative Examples and the Examples is by weight percentage. Further, the compounds used in the Examples and Comparative Examples are expressed by the symbols as shown below.

Indication of the compounds using the symbols

$$R-(A_1)-Z_2 \text{------} Z_n-(A_n)-S$$

| | Symbol |
|---|---|
| 1) Left terminal group R— | |
| $C_nH_{2n+1}-$ | n- |
| $C_nH_{2n+1}O-$ | nO— |
| $C_nH_{2n+1}OC_mH_{2m}-$ | nOm- |
| $CH_2=CHC_nH_{2n}-$ | Vn- |
| $C_nH_{2n+1}CH=CHC_mH_{2m}-$ | nVm- |
| $C_nH_{2n+1}CH=CHC_mH_{2m}CH=CHC_kH_{2k}-$ | nVmVk- |
| 2) Ring structure $-(A_1)-, -(A_n)-$ | |
| 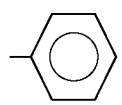 | B |
| 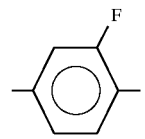 | B(F) |

-continued

R—(A₁)—Z₂ ———————— Zₙ—(Aₙ)—S

| Structure | Symbol |
|---|---|
| 1,4-phenylene with 2,5-F substituents | B(F,F) |
| cyclohexylene | H |
| pyrimidine | Py |
| dioxane | D |
| cyclohexenylene | Ch |

3) Linking group —Z₁—, —Zₙ—

| | |
|---|---|
| —CH₂CH₂— | 2 |
| —COO— | E |
| —C≡C— | T |
| —CH=CH— | V |
| —CF₂O— | CF2O |
| —OCF₂— | OCF2 |

4) Right terminal group —X

| | |
|---|---|
| —F | —F |
| —Cl | —CL |
| —CN | —C |
| —CF₃ | —CF3 |
| —OCF₃ | —OCF3 |
| —OCF₂H | —OCF2H |
| —CₙH₂ₙ₊₁ | -n |
| —OCₙH₂ₙ₊₁ | —On |
| —COOCH₃ | —EMe |
| —CₙH₂ₙCH=CH₂ | -nV |
| —CₘH₂ₘCH=CHCₙH₂ₙ₊₁ | -mVn |

5) Example of indication

Example 1  3-H2B(F,F)B(F)—F

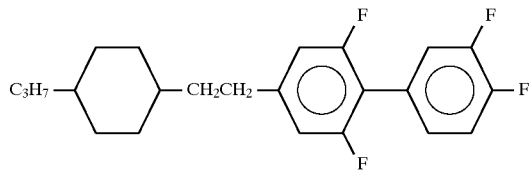

Example 2  3-HB(F)TB-2

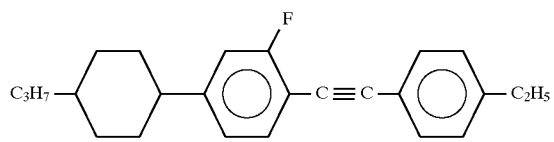

-continued

R—(A₁)—Z₂ ———— Zₙ—(Aₙ)—S  Symbol

Example 3  1V2-BEB(F,F)—C

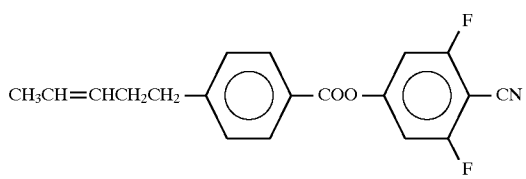

The characteristic data of the liquid crystal compositions are shown by the upper limit of the nematic phase transition temperature (clearing point: $T_{NI}$), the lower limit of the nematic phase transition temperature ($T_L$), viscosity ($\eta_{20}$) at 20° C., optical anisotropy ($\Delta n$) at 25° C., dielectric anisotropy ($\Delta\epsilon$) at 25° C. and threshold voltage ($V_{th}$) at 20° C. The determination of the voltage holding rate was carried out at 25° C. in accordance with the area method. The $T_L$ point was judged by the liquid crystal phase after allowing to stand for 30 days in a freezer at 0° C., –10° C., –20° C. and –30° C., respectively.

Comparative Example 1

The following composition disclosed in Example 2 of Japanese Patent Kokai 2-233626 was prepared.

| | |
|---|---|
| 3-HHB(F,F)-F | 15.0% |
| 2-HHB(F)-F | 28.4% |
| 3-HHB(F)-F | 28.3% |
| 5-HHB(F)-F | 28.3% |
| $T_{NI}$ = 110.7° C. | |
| $T_{SN}$ < 0° C. | |
| $\eta_{20}$ = 25.0 mPa · s | |
| $\Delta n$ = 0.077 | |
| $V_{th}$ = 2.32 (V) | |
| V.H.R. = 98.8% | |

This liquid crystal composition has high threshold voltage and poor compatibility at low temperature ($T_L$ is high).

Comparative Example 2

The following composition disclosed in Example 1 of WO 94/03558 was prepared.

| | |
|---|---|
| 7-HB(F,F)-F | 10.0% |
| 2-HHB(F,F)-F | 25.0% |
| 3-HHB(F,F)-F | 35.0% |
| 5-HHB(F,F)-F | 18.0% |
| 7-HB(F)-F | 12.0% |
| $T_{NI}$ = 42.9° C. | |
| $T_{SN}$ < 0° C. | |
| $\eta_{20}$ = 22.2 mPa · s | |
| $\Delta n$ = 0.059 | |
| $V_{th}$ = 1.07 V | |
| V.H.R. = 98.7% | |

This liquid crystal composition has low threshold voltage, but low clearing point and poor compatibility at low temperature. Further, it has low $\Delta n$ and lacks practicality.

Comparative Example 3

The following composition disclosed in Example 2 of WO 94/03558 was prepared.

| | |
|---|---|
| 2-HHB(F,F)-F | 26.0% |
| 3-HHB(F,F)-F | 26.0% |
| 5-HHB(F,F)-F | 26.0% |
| 7-HB(F)-F | 12.0% |
| 5-H2B(F)-F | 10.0% |
| $T_{NI}$ = 46.0° C. | |
| $T_{SN}$ < 0° C. | |
| $\eta_{20}$ = 21.6 mPa · s | |
| $\Delta n$ = 0.058 | |
| $V_{th}$ = 1.17 V | |
| V.H.R. = 98.5% | |

This liquid crystal composition has low threshold voltage, but low clearing point and poor compatibility at low temperature. Further, it has low $\Delta n$ and lacks practicality.

EXAMPLE 1

| | |
|---|---|
| 2-HB(F)EB(F,F)-F | 5.0% |
| 5-HB(F)EB(F,F)-F | 5.0% |
| 3-HHB(F,F)-F | 10.0% |
| 4-HHB(F,F)-F | 5.0% |
| 3-H2HB(F,F)-F | 12.0% |
| 4-H2HB(F,F)-F | 10.0% |
| 5-H2HB(F,F)-F | 10.0% |
| 3-HH2B(F,F)-F | 15.0% |
| 5-HH2B(F,F)-F | 10.0% |
| 3-HBB(F,F)-F | 12.0% |
| 5-HBB(F,F)-F | 6.0% |
| $T_{NI}$ = 78.3° C. | |
| $T_{SN}$ < 30° C. | |
| $\eta_{20}$ = 30.5 mPa · s | |
| $\Delta n$ = 0.086 | |
| $\Delta\epsilon$ = 10.5 | |
| $V_{th}$ = 1.49 V | |
| V.H.R. = 98.7% | |

This liquid crystal composition has excellent compatibility at low temperature, broad nematic phase range and low threshold voltage. Further, it has reasonably high $\Delta n$ and is of great practical use.

EXAMPLE 2

| | |
|---|---|
| 3-HB(F)EB(F,F)-F | 5.0% |
| 3-HHB(F,F)-F | 10.0% |
| 5-HHB(F,F)-F | 5.0% |
| 3-H2HB(F,F)-F | 10.0% |
| 5-H2HB(F,F)-F | 12.0% |
| 3-HH2B(F,F)-F | 12.0% |
| 5-HH2B(F,F)-F | 7.0% |
| 3-HBB(F,F)-F | 12.0% |

-continued

| | |
|---|---|
| 5-HBB(F,F)-F | 12.0% |
| 3-H2BB(F,F)-F | 7.0% |
| 5-H2BB(F,F)-F | 8.0% |
| $T_{NI}$ = 74.0° C. | |
| $T_{SN}$ < 30° C. | |
| $\eta_{20}$ = 28.5 mPa · s | |
| $\Delta n$ = 0.097 | |
| $\Delta \epsilon$ = 9.8 | |
| $V_{th}$ = 1.55 V | |
| V.H.R. = 98.8% | |

EXAMPLE 3

| | |
|---|---|
| 2-HB(F)EB(F,F)-F | 7.0% |
| 3-HB(F)EB(F,F)-F | 5.0% |
| 5-HB(F)EB(F,F)-F | 8.0% |
| 3-HHB(F,F)-F | 10.0% |
| 4-HHB(F,F)-F | 5.0% |
| 3-H2HB(F,F)-F | 8.0% |
| 4-H2HB(F,F)-F | 7.0% |
| 5-H2HB(F,F)-F | 7.0% |
| 3-HH2B(F,F)-F | 10.0% |
| 5-HH2B(F,F)-F | 5.0% |
| 3-HBB(F,F)-F | 14.0% |
| 5-HBB(F,F)-F | 14.0% |
| $T_{NI}$ = 70.1° C. | |
| $T_{SN}$ < 30° C. | |
| $\eta_{20}$ = 36.2 mPa · s | |
| $\Delta n$ = 0.093 | |
| $\Delta \epsilon$ = 12.4 | |
| $V_{th}$ = 1.25 V | |
| V.H.R. = 98.4% | |

EXAMPLE 4

| | |
|---|---|
| 2-HB(F)EB(F,F)-F | 5.0% |
| 3-HB(F)EB(F,F)-F | 4.0% |
| 3-HHB(F,F)-F | 10.0% |
| 4-HHB(F,F)-F | 5.0% |
| 3-H2HB(F,F)-F | 7.0% |
| 5-H2HB(F,F)-F | 8.0% |
| 3-HH2B(F,F)-F | 9.0% |
| 5-HH2B(F,F)-F | 9.0% |
| 3-HBB(F,F)-F | 15.0% |
| 5-HBB(F,F)-F | 15.0% |
| 3-HBEB(F)F)-F | 3.0% |
| 3-HHEB(F,F)-F | 10.0% |
| $T_{NI}$ = 75.6° C. | |
| $T_{SN}$ < 30° C. | |
| $\eta_{20}$ = 32.5 mPa · s | |
| $\Delta n$ = 0.095 | |
| $\Delta \epsilon$ = 11.2 | |
| $V_{th}$ = 1.32 V | |
| V.H.R. = 98.3% | |

EXAMPLE 5

| | |
|---|---|
| 3-HB(F)EB(F,F)-F | 5.0% |
| 5-HB(F)EB(F,F)-F | 9.0% |
| 7-HB(F,F)-F | 6.0% |
| 3-HHB(F,F)-F | 9.0% |
| 3-H2HB(F,F)-F | 12.0% |
| 5-H2HB(F,F)-F | 10.0% |
| 3-HH2B(F,F)-F | 15.0% |
| 5-HH2B(F,F)-F | 10.0% |
| 3-HBB(F,F)-F | 12.0% |
| 5-HBB(F,F)-F | 12.0% |
| $T_{NI}$ = 67.4° C. | |
| $T_{SN}$ < 30° C. | |

| | |
|---|---|
| $\eta_{20}$ = 29.7 mPa · s | |
| $\Delta n$ = 0.088 | |
| $\Delta \epsilon$ = 10.9 | |
| $V_{th}$ = 1.35 V | |
| V.H.R. = 98.6% | |

EXAMPLE 6

| | |
|---|---|
| 2-HB(F)EB(F,F)-F | 4.0% |
| 3-HB(F)EB(F,F)-F | 3.0% |
| 5-HB(F)EB(F,F)-F | 4.0% |
| 3-HHB(F,F)-F | 9.0% |
| 4-HHB(F,F)-F | 4.0% |
| 3-H2HB(F,F)-F | 10.0% |
| 5-H2HB(F,F)-F | 10.0% |
| 3-HH2B(F,F)-F | 10.0% |
| 5-HH2B(F,F)-F | 7.0% |
| 3-HBB(F,F)-F | 11.0% |
| 5-HBB(F,F)-F | 11.0% |
| 5-H2BB(F,F)-F | 10.0% |
| 3-HHBB(F,F)-F | 3.0% |
| 3-HH2BB(F,F)-F | 4.0% |
| $T_{NI}$ = 84.4° C. | |
| $T_{SN}$ < 30° C. | |
| $\eta_{20}$ = 33.4 mPa · s | |
| $\Delta n$ = 0.101 | |
| $\Delta \epsilon$ = 11.3 | |
| $V_{th}$ = 1.49 V | |
| V.H.R. = 98.6% | |

EXAMPLE 7

| | |
|---|---|
| 2-HB(F)EB(F,F)-F | 5.0% |
| 5-HB(F)EB(F,F)-F | 5.0% |
| 7-HB(F,F)-F | 9.0% |
| 3-HHB(F,F)-F | 10.0% |
| 3-H2HB(F,F)-F | 6.0% |
| 3-HH2B(F,F)-F | 7.0% |
| 5-HH2B(F,F)-F | 5.0% |
| 3-HBB(F,F)-F | 18.0% |
| 5-HBB(F,F)-F | 18.0% |
| 3-HHEB(F,F)-F | 5.0% |
| 5-HHEB(F,F)-F | 4.0% |
| 3-HH2BB(F,F)-F | 4.0% |
| 5-HH2BB(F,F)-F | 4.0% |
| $T_{NI}$ = 70.3° C. | |
| $T_{SN}$ < 30° C. | |
| $\eta_{20}$ = 32.3 mPa · s | |
| $\Delta n$ = 0.095 | |
| $\Delta \epsilon$ = 12.5 | |
| $V_{th}$ = 1.33 V | |
| V.H.R. = 98.5% | |

EXAMPLE 8

| | |
|---|---|
| 5-HB(F,F)EB(F,F)-F | 5.0% |
| 3-HHB(F)EB(F,F)-F | 6.0% |
| 7-HB(F,F)-F | 2.0% |
| 3-H2HB(F,F)-F | 5.0% |
| 5-H2HB(F,F)-F | 5.0% |
| 3-HH2B(F,F)-F | 5.0% |
| 3-HBB(F,F)-F | 27.0% |
| 5-HBB(F,F)-F | 27.0% |
| 5-HBEB(F,F)-F | 3.0% |
| 3-HHEB(F,F)-F | 10.0% |
| 5-HHEB(F,F)-F | 5.0% |
| $T_{NI}$ = 71.7° C. | |
| $T_{SN}$ < 30° C. | |
| $\eta_{20}$ = 39.1 mPa · s | |

```
Δn = 0.106
Δε = 11.2
V_th = 1.21 V
V.H.R. = 98.5%
```

INDUSTRIAL UTILIZATION

As shown in the Examples and Comparative Examples, the present invention can provide the liquid crystal compositions having low threshold voltage, excellent compatibility at low temperature and broad nematic phase range, while satisfying various characteristics required for the liquid crystal composition for AM-LCD.

We claim:

1. A liquid crystal composition which comprise as a first component at least one or more compounds represented by formula (1')

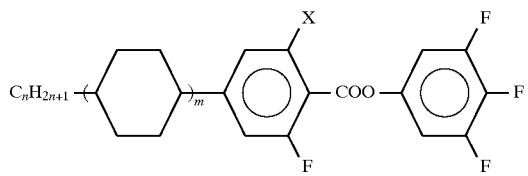

wherein n represents an integer of 1–10; X represents H or F; or m represents 1 or 2, and as a second component at least one or more compounds represented by formulas (2-1) to (2-5) in which n represents an integer of 1–10.

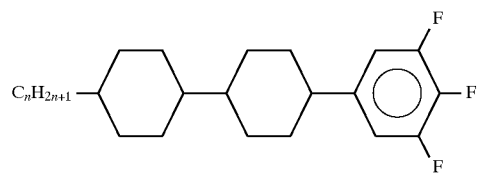

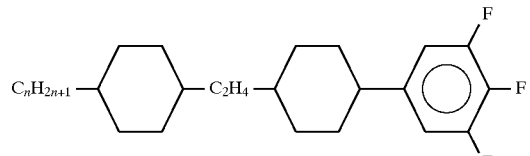

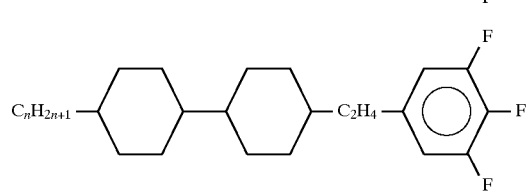

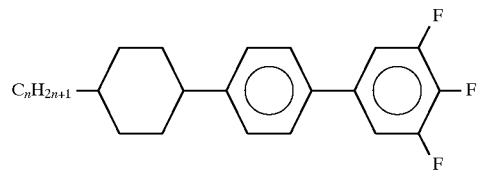

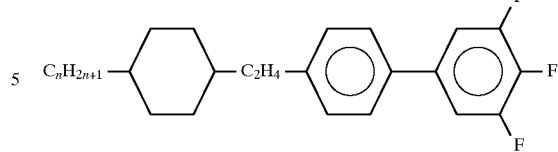

2. The liquid crystal composition set forth in claim 1 wherein the first component is 3–40% by weight and the second component is 50–97% by weight, based on the total weight of the liquid crystal composition.

3. The liquid crystal composition of claim 1 further comprising a compound represented by formula (3-1) and/or a compound represented by formula 3-2)

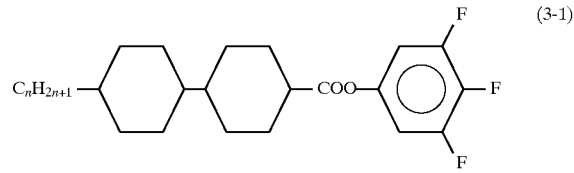

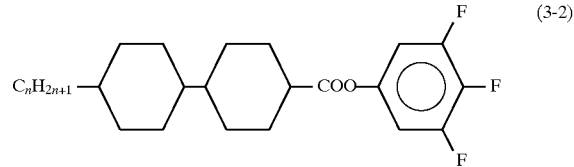

in which n represents an integer of 1–10.

4. The liquid crystal composition of claim 1 further comprising the compound represented by formula (4)

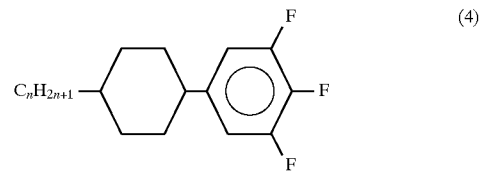

in which n represents an integer of 1–10.

5. The liquid crystal composition of claim 1 further comprising a compound represented by formula (5-1) and/or a compound represented by formula (5-2)

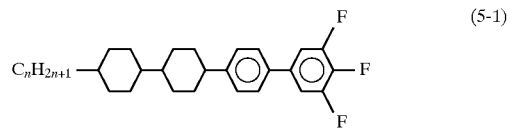

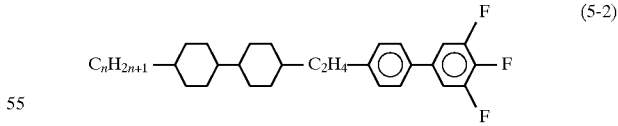

in which n represents an integer of 1–10.

6. A liquid crystal display element comprising the liquid crystal composition set forth in claim 1.

7. The liquid crystal composition as claimed in claim 1, comprising a compound represented by formula (2-1).

8. The liquid crystal composition as claimed in claim 1, comprising a compound represented by formula (2-2).

9. The liquid crystal composition as claimed in claim 1, comprising a compound represented by formula (2-3).

10. The liquid crystal composition as claimed in claim 1, comprising a compound represented by formula (2-4).

11. The liquid crystal composition as claimed in claim 1, comprising a compound represented by formula (2-5).

12. The liquid crystal composition as claimed in claim 3, comprising a compound represented by formula (3-1).

13. The liquid crystal composition as claimed in claim 3, comprising a compound represented by formula (3-2).

14. The composition as claimed in claim 5, comprising a compound represented by formula (5-1).

15. The composition as claimed in claim 5, comprising a compound represented by formula (5-2).

16. A liquid crystal display element comprising the liquid crystal composition set forth in claim 2.

17. A liquid crystal display element comprising the liquid crystal composition set forth in claim 3.

18. A liquid crystal display element comprising the liquid crystal composition set forth in claim 4.

19. A liquid crystal display element comprising the liquid crystal composition set forth in claim 5.

* * * * *